United States Patent [19]

Caradonna

[11] 4,244,368
[45] Jan. 13, 1981

[54] INCONTINENT GARMENT

[75] Inventor: Peter W. Caradonna, Holliston, Mass.

[73] Assignee: Gilman Brothers Inc., Boston, Mass.

[21] Appl. No.: 17,549

[22] Filed: Mar. 5, 1979

[51] Int. Cl.$^3$ .............................................. A41B 13/02
[52] U.S. Cl. .................................................. 128/287
[58] Field of Search ............................... 128/287, 288

[56] References Cited

U.S. PATENT DOCUMENTS

| | | | |
|---|---|---|---|
| 2,604,097 | 7/1952 | White | 128/287 |
| 2,606,558 | 8/1952 | Kennette | 128/287 |
| 3,049,124 | 8/1962 | Thompson | 128/287 |
| 3,088,462 | 5/1963 | Muto | 128/288 |
| 3,315,677 | 4/1967 | Tyrrell, Jr. | 128/288 |
| 3,407,813 | 10/1968 | Grippo et al. | 128/287 |
| 4,023,571 | 5/1977 | Comerford et al. | 128/288 |

Primary Examiner—Robert W. Michell
Assistant Examiner—C. F. Rosenbaum
Attorney, Agent, or Firm—Edward F. Levy

[57] ABSTRACT

An incontinent garment is constructed to selectively mount either a disposable liner or a reusable liner interchangeably, without discomfort to the wearer. The garment body has male snap fastener elements arranged along its upper edge for receiving mating female snap fasteners carried by reusable liners. The garment body is also adapted to mount a disposable liner by means of self-adhering strips, leaving the male snap fastener elements exposed for contact with the wearer's body. The garment also includes separate auxiliary straps mounting female snap fasteners arranged to engage with and cover over the male snap fasteners when a disposable liner is mounted in the garment.

3 Claims, 4 Drawing Figures

U.S. Patent  Jan. 13, 1981  4,244,368
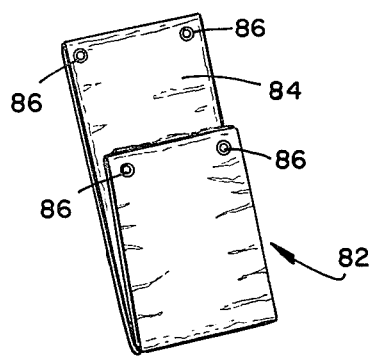
FIG. 3
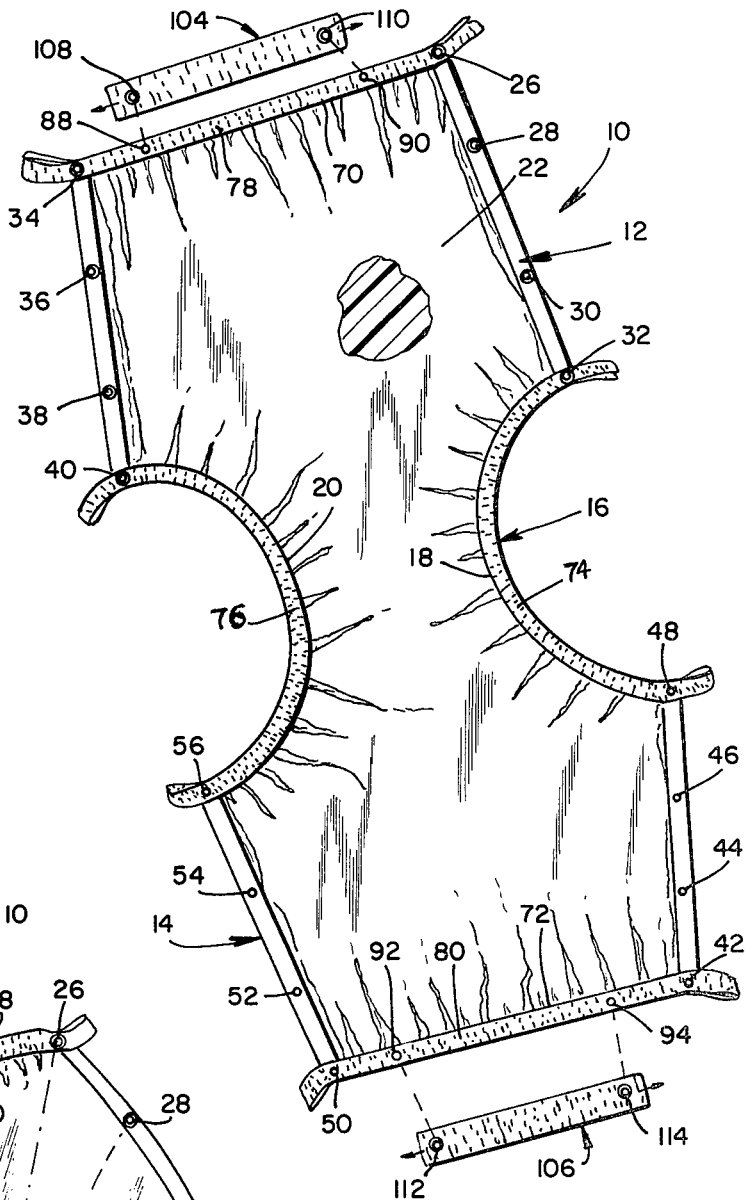
FIG. 1
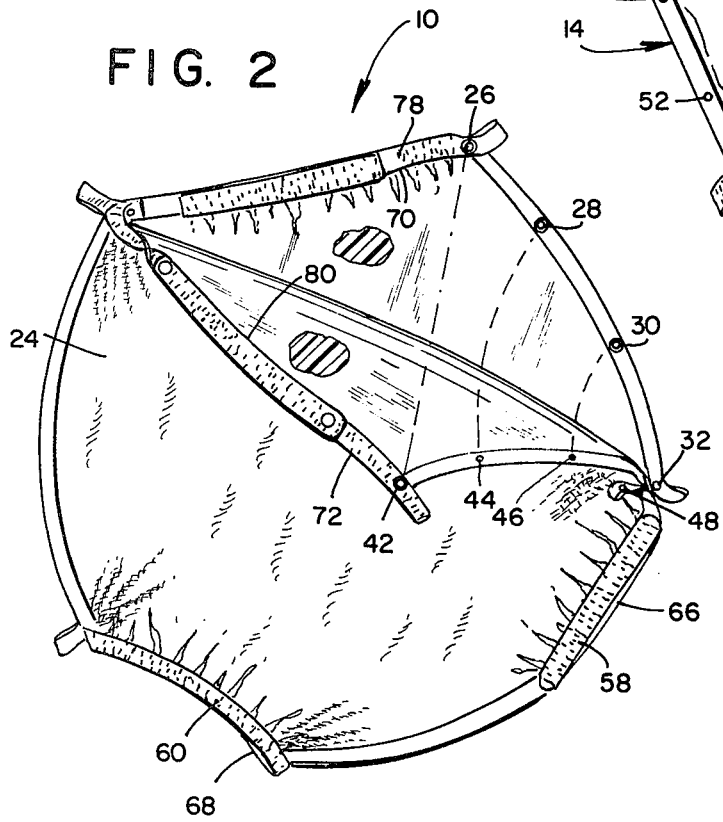
FIG. 2
FIG. 4

INCONTINENT GARMENT

The present invention relates to improvements in incontinent garments, and in particular relates to an incontinent garment adapted to permit a disposable liner or a reusable liner to be mounted therein, selectively and interchangeably, without discomfort to the wearer.

Incontinent garments are devices used by patients generally who cannot control their body functions and in essence can be classified as diapers for adults. Such garments are in the form of a pant or body portion arranged to conveniently fit patients of various sizes, shapes and dimensions. These pants or body portions carry liners made of flannel, Olefin, or other types of absorbent materials.

The liners for incontinent garments are adapted to be removably and replaceably mounted therein, and generally come in two varieties, one a reusable type and the other a disposable type. In the case where a disposable liner is used, the liner is suitably attached to the support by adhesive means carried by and forming a part of the liner. On the other hand the reusable liner has female snap fasteners attached thereto and positioned for snap attachment to male counter-part snap fasteners carried by the pant or body portion.

Heretofore separate type garments or supports have been manufactured and supplied for carrying the different liners, one type for carrying a reusable liner and another type for carrying a disposable liner. In the garment supplied for use with disposable liners, the garment was devoid of fasteners, and in the garment supplied for use with reusable liners, the garment was supplied with snap fastener elements for supporting the liner. In these conventional incontinent garments, the garment designed to mount disposable liners by means of adhesive strips carried by the liners, could not mount a reusable liner since it had no snap fasteners. On the other hand, the garment designed to mount reusable liners could not be used to mount disposable liners, since the latter, when adhesively mounted, did not cover over the male snap fasteners on the garment, and these exposed snap fasteners would press into the wearer's body when the garment was worn, causing discomfort.

Consequently, it has been necessary to manufacture incontinent garments of two different types, each in a variety of sizes, and retail establishments have had to carry a double stack of garments, one type for disposable liners and another type for reusable liners.

To obviate this and other limitations in the use of the conventional incontinent garments, the present invention provides a single incontinent garment which is adapted to receive and mount either a disposable liner or a reusable liner without any discomfort to the wearer. The garment is made with inwardly-projecting male snap fasteners around its waist portion for attachment to the female snap fasteners of reusable liners. In accordance with the present invention, these projecting male snap fasteners are neutralized when the garment is used to mount a disposable liner. This is accomplished by means of a protective straps each having female snap fasteners disposed to match and fit the male snap fasteners carried by the garment so that there is no longer any exposure to the male snap protrusions. These neutralizing straps are not required and may be removed when use of the reusable liners is contemplated. By the foregoing approach, not only is discomfort to the user alleviated, but the need to carry separate garments for the different liners is eliminated. Hence required inventory and space needs are minimized, thereby providing considerable savings to both the supplier and the retailer.

It is therefore a principal object of the invention to provide an incontinent garment which is adapted to removably mount either a disposable liner or a reusable liner, as desired without any discomfort to the wearer.

Another object of the invention is the provision of an incontinent garment of the type described which improves the comfort of the user, reduces the inventory required to carry separate type garments, decreases costs and makes more efficient use of space where such garments are stored.

Additional objects and advantages of the invention will become apparent during the course of the following specification when taken in connection with the accompanying drawings, in which:

FIG. 1 is a plan view of an incontinent garment made in accordance with the present invention, the garment being shown in open condition with the protective straps shown disconnected therefrom;

FIG. 2 is a plan view of the garment of FIG. 1 shown in its partially closed condition, with the protective straps shown mounted thereon;

FIG. 3 is a plan view of a typical reusable liner having female snap fasteners thereon and shown in folded condition; and FIG. 4 is a plan view of a pair of typical disposable liners, showing the front and rear surfaces thereof.

Referring in detail to the drawings, there is shown in FIG. 1 an incontinent garment pant or body portion 10 shown in the open, flattened condition to which it is brought when an absorbent removable liner is to be attached thereto. The garment 10 is generally of conventional construction, having relatively wide end panels 12 and 14 joined by a central section 16. The central section 16 is of narrower width, being formed with generally semi-circular side edges 18 and 20 which form leg openings when the garment is assembled.

The garment 10 has a vinyl coated inner surface 22 which faces the wearer's body when the garment is in use. The outer surface 24 of the garment may be fabric. Along the side edges of the end panel 12 are mounted spaced female snap fasteners 26, 28, 30, 32, 34, 36, 38 and 40 which face the inner surface 22 of the garment. Along the side edges of the end panel 14 are mounted male snap fasteners 42, 44, 46, 48, 50, 52, 54 and 56 which face the outer surface of the garment and which are located to match the aforesaid female snap fasteners 26–40 for respective attachment thereto in assembling the garment. After the removable liner is mounted in the garment, the garment is assembled about the body of the wearer by snapping together the mating male and female snap fasteners along the sides of the end panels 12 and 14.

FIG. 2 shows the garment 10 partially assembled with the female snap fasteners 34, 36, 38 and 40 at one side of the garment attached to the respective female snap fasteners 50, 52, 54 and 56 at the same side of the garment. This view also indicates the manner in which the female snap fasteners 26, 38, 30 and 32 at the other side of the garment are attached to the respective male snap fasteners 42, 44, 46 and 48. In the completed garment, the arcuate side edges 16 and 20 of the central section 16 form respective leg openings 66 and 68, while the free end edges 70 and 72 of the end panels 12 and 14 form a waist opening.

The arcuate side edges 18 and 20 of the central section 16 are bordered with respective elastic fabric tape strips 74 and 76 which are stretchable, so that the leg openings 66 and 68, formed thereby in the assembled garment, fit snugly about the thighs of the wearer, with the central section 16 serving as the crotch portion of the wearer. Similarly, the free end edges 70 and 72 of the end panels 12 and 14 are bordered by respective elastic fabric tape strips 78 and 80 which provide a stretchable waist band in the assembled garment.

The garment 10 is adapted to mount a reusable liner 82, which is shown in FIG. 3. The reusable liner 82 is of the conventional type which is commercially available, and consists of an absorbent body 84 made of flannel, Olefin, or other absorbent material which may be washed and re-used. At the corners of the body 84 are mounted female snap fasteners 86. For the purpose of removably attaching the reusable liner 78 to the garment 10, the latter is provided with a pair of male snap fasteners 88 and 90 spaced along the elastic strip 78, and a pair of male snap fasteners 92 and 94 spaced along the elastic strip 80. These male snap fasteners 88, 90, 92 and 94 project from the inner garment surface 22 and their protrusions face the body of the wearer when the garment is assembled and worn.

The garment 10 is also adapted to mount a disposable liner 96, two of which are shown in FIG. 4. The disposable liner is of commercially-available conventional type having a paper body portion 98 coated on one surface with a pad 100 of fluffy absorbent material. On the opposite surface of the body portion 98 is a strip of pressure-sensitive adhesive 102. When it is desired to mount a disposable liner in the garment 10, the disposable liner 96 is centered on the inner surface 22 of the garment body, and the adhesive strip 102 is pressed against said inner surface so that it adheres thereto with the absorbent pad 100 facing outwardly. The disposable liner 96 is conventionally made of a length shorter than the length of the opened garment 10, so that in its mounted position, the liner 96 does not cover over the male snap fasteners 88, 90, 92 and 94 at the waist-band of the garment. Thus, if the garment were to be worn in this condition, the exposed male snap fasteners 88, 90, 92 and 94 would project inwardly and bite into the flesh at the waist of the wearer, causing considerable discomfort. Consequently, a garment such as the garment 10 is conventionally not used with disposable liners, and if it is desired to use disposable liners, a separate garment without the male snap fasteners 88, 90, 92 and 94 would be provided and used for this purpose.

In accordance with the invention herein, in order to permit the garment 10 to be used with both reusable liners and disposable liners, the garment is provided with a pair of removable fabric strips or tapes 104, 106. Mounted at the ends of strip 104 are a pair of female snap fasteners 108 and 110 which are positioned to engage and attach to the male snap fasteners 88 and 90 on garment 10. Mounted at the ends of strip 106 are a pair of female snap fasteners 112 and 114 which are positioned to engage and attach to the male snap fasteners 92 and 94 at the other end of the garment.

The garment 10 is supplied with the strips 104 and 106 attached thereto, in the manner shown in FIG. 2. The strips 104 and 106 cover over the exposed male fasteners 88, 90, and 92, 94, respectively, so that the protrusions of these male snap fasteners are in effect neutralized, and when the garment is worn with a disposable liner 96 adhesively attached therein, the male snap fasteners do not cause discomfort to the wearer. The outer surfaces of the strips 104 and 106 are smooth and do not irritate the skin of the wearer.

When the garment is to be used to mount a reusable liner 82, the strips 104 and 106 are detached and removed from the garment. This exposes the male snap fasteners 88, 90, 92 and 94, and the reusable liner may be attached thereto in the usual manner. Thus a single incontinent garment 10 is now adapted to be used as a comfortable mount for both reusable liners and disposable liners.

The protective strips 104 and 106 are made of elastic fabric material and are stretchable in a longitudinal direction. The strips 104 and 106 in mounted condition may therefore stretch to the same degree as the waistband elastic tape strips 78 and 80 when the garment is being worn.

While a preferred embodiment of the invention has been shown and described herein, it is obvious that numerous omissions, changes and additions may be made in such embodiments without departing from the spirit and scope of the invention.

What is claimed is:

1. An incontinent garment for removably mounting disposable liners and alternately and selectively mounting reusable liners by means of female snap fasteners secured to said reusable liners, said garment comprising
  a pant body having a waist portion,
  a first pair of spaced male snap fasteners mounted at the front of said waist portion and a second pair of spaced male snap fasteners mounted at the rear of said waist portion, said snap fasteners being positioned to receive the female snap fasteners of said reusable liners for removably mounting the latter within the body, said male snap fasteners having protrusions facing inwardly of said pant body,
  and neutralizing means removably attached to said male snap fasteners to cover over the protrusions thereof when a disposable liner is mounted in said garment in the absence of a reusable liner therein,
  said neutralizing means comprising a pair of flexible straps each having a pair of spaced female snap fasteners mounted thereon and positioned to attach to and cover over the respective first and second pairs of male snap fasteners on said waist portion, and having a smooth outer surface facing the interior of said garment,
  said disposable liners including adhesive means for attachment thereof to said garment, said disposable liners in attached position leaving said male snap fasteners exposed with their protrusions facing the body of the wearer, said flexible straps being attachable to said exposed male snap fasteners to cover over the latter when a disposable liner is attached to said garment.

2. An incontinent garment according to claim 1 in which said neutralizing means comprises a plurality of flexible straps having female snap fasteners mounted thereon and positioned to attach to and cover over said male snap fasteners.

3. An incontinent garment according to claim 1 in which said waist portion includes a waist band of stretchable elastic tape, said male snap fasteners being mounted on said tape, said straps being also made of stretchable elastic tape.

* * * * *